(12) United States Patent
Quinn et al.

(10) Patent No.: US 12,290,460 B2
(45) Date of Patent: May 6, 2025

(54) STENT AND ASSOCIATED SYSTEMS AND METHODS

(71) Applicant: BOSTON SCIENTIFIC SCIMED, INC., Maple Grove, MN (US)

(72) Inventors: James Quinn, Galway (IE); Ryan Desmond Lynch, Roscommon (IE); Gerard Duignan, Galway (IE); Darren Gerard Curran, Galway (IE); Sean P Fleury, Princeton, MA (US); Peter L Dayton, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 367 days.

(21) Appl. No.: 17/732,106

(22) Filed: Apr. 28, 2022

(65) Prior Publication Data

US 2022/0346998 A1 Nov. 3, 2022

Related U.S. Application Data

(60) Provisional application No. 63/181,618, filed on Apr. 29, 2021.

(51) Int. Cl.
*A61F 5/00* (2006.01)
*A61B 17/04* (2006.01)
(Continued)

(52) U.S. Cl.
CPC ........ *A61F 5/0079* (2013.01); *A61B 17/0401* (2013.01); *A61B 17/1114* (2013.01); *A61F 5/0089* (2013.01); *A61F 2002/045* (2013.01)

(58) Field of Classification Search
CPC .................. A61F 5/0079; A61F 5/0089; A61F 2002/045; A61F 2002/068;
(Continued)

(56) References Cited

U.S. PATENT DOCUMENTS

| 8,114,045 B2 | 2/2012 | Surti |
| 9,155,650 B2 | 10/2015 | Birk |

(Continued)

FOREIGN PATENT DOCUMENTS

WO 2020060932 A1 3/2020

OTHER PUBLICATIONS

International Search Report and Written Opinion dated Jul. 28, 2022 for International Application No. PCT/US2022/026785.

*Primary Examiner* — Tan-Uyen T Ho
*Assistant Examiner* — Cherie M Poland
(74) *Attorney, Agent, or Firm* — Seager, Tufte & Wickhem, LLP

(57) ABSTRACT

A mesh element having a mesh gauge selected to control flow of materials therethrough. The mesh element is implantable into an anatomical structure upstream of a body passage or within a body passage to control flow of materials through the body passage. The mesh element may be coupled to a support structure to facilitate anchoring of the mesh element in place relative to the body passage. The support structure may have a lumen defined therethrough to allow flow of materials through the body passage, with the mesh element regulating the flow of materials into the lumen. The mesh element alternatively may be directly coupled to an anatomical structure upstream of a body passage to regulate or determine flow of materials through the body passage.

20 Claims, 8 Drawing Sheets

(51) Int. Cl.
*A61B 17/11* (2006.01)
*A61F 2/04* (2013.01)

(58) Field of Classification Search
CPC .. A61F 2002/8486; A61F 2/04; A61F 2/2476; A61F 2/848; A61F 2250/006; A61F 2250/0017; A61F 2250/0023; A61F 2250/0039; A61F 2250/0062; A61F 2220/0025; A61F 2220/0083; A61B 17/0401; A61B 17/1114
See application file for complete search history.

(56) References Cited

U.S. PATENT DOCUMENTS

| | | |
|---|---|---|
| 9,833,343 B2 | 12/2017 | Burnside et al. |
| 10,736,764 B2 | 8/2020 | Dean et al. |
| 2008/0221595 A1 | 9/2008 | Sutri |
| 2013/0030351 A1 | 1/2013 | Belhe et al. |
| 2014/0276336 A1* | 9/2014 | Sharma ................. A61F 5/0076 604/8 |
| 2014/0350694 A1* | 11/2014 | Behan .................... A61F 2/966 623/23.65 |
| 2020/0015990 A1 | 1/2020 | Sharma et al. |

* cited by examiner

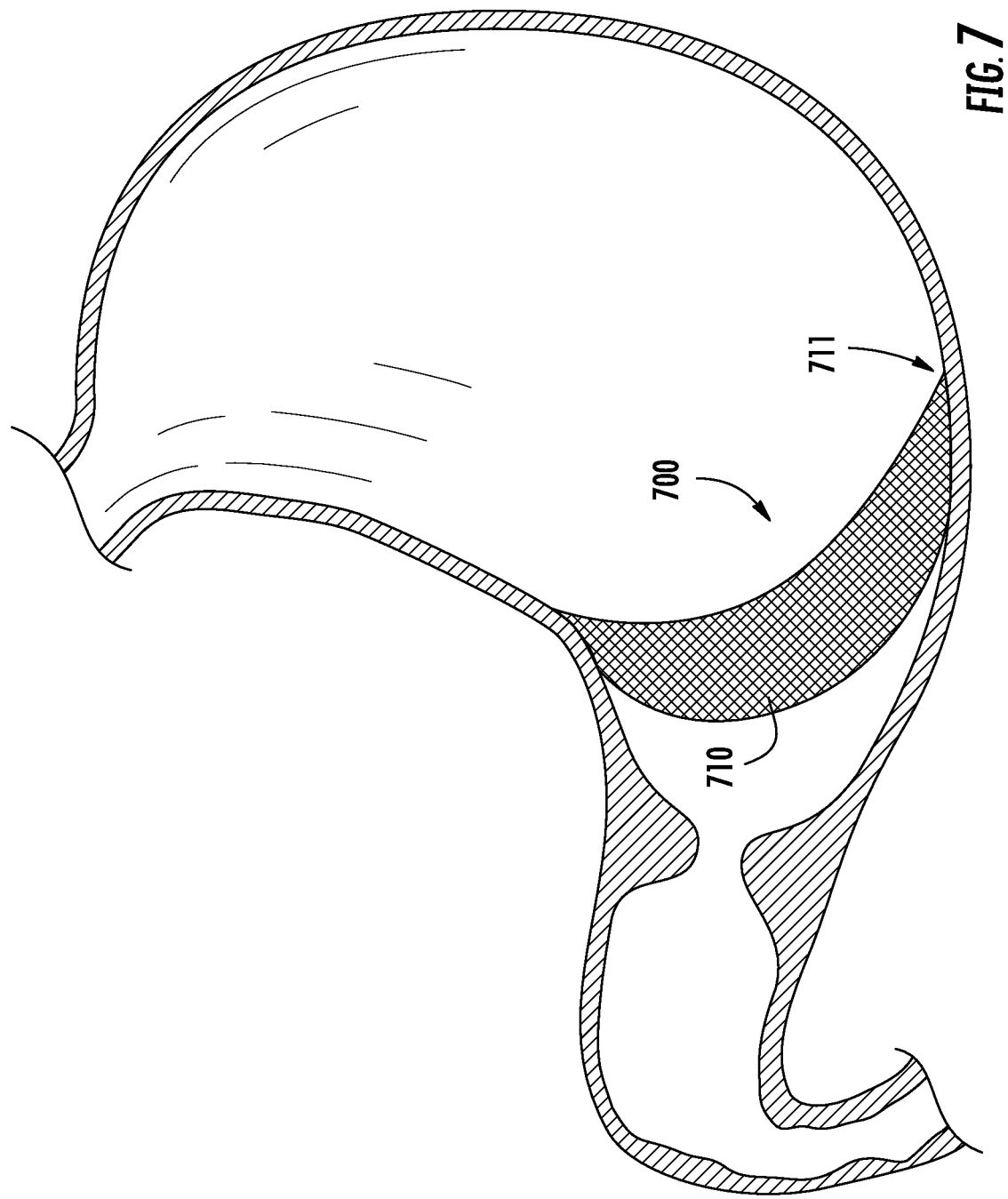

STENT AND ASSOCIATED SYSTEMS AND METHODS

PRIORITY

The present application is a non-provisional of, and claims the benefit of priority under 35 U.S.C. § 119 to, U.S. Provisional Application No. 63/181,618, filed Apr. 29, 2021, the disclosure of which is hereby incorporated by reference herein in its entirety and for all purposes.

FIELD

The present disclosure relates generally to the field of implantable medical devices, systems, and methods for regulating passage of materials through a body opening. More particularly, the present disclosure relates to devices, systems, and methods for adjusting passage of materials through a pylorus.

BACKGROUND

Duodenal occlusion, such as by occluding or partially occluding the pylorus, which leads from the stomach to the duodenum, has become a common treatment for various gastric procedures, such as bariatric procedures such as gastric bypasses. Bypass procedures such as gastrojejunostomies bypass a section of the small intestine, such as by preventing passage of gastric materials (e.g., fluids, chyme, etc.) through the pylorus into the duodenum and by redirecting the flow of gastric materials through an anastomosis into the jejunum. Other bariatric treatments involve slowing gastric emptying (the flow of material, such as fluids or chyme, from the stomach to the duodenum), with consequent inducement of a feeling of fullness or satiety which may lead to reduction of food intake and associated weight loss. Stents have modified from their original purpose of supporting a structure to be used in a variety of such procedures. Thus, instead of using a stent configured to hold open a passage, stents have been modified to close a passage. Various challenges are presented by such modifications, such as migration due to impact of forces from materials which generally flow through the passage through the stent and are now blocked by the stent. Moreover, certain procedures may require modification of the flow of materials through the stent. For instance, the implemented therapy of occluding the pylorus may be working, and increased passage of food through the pylorus may be medically indicated. Alternatively, increased blockage may be medically indicated. A flow-regulating device which resists migration from its deployment site and/or allows for adjustment of the rate of flow of materials therethrough would be welcome in the art.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a device for regulating flow of materials through a body passage is provided.

In accordance with one aspect of the present disclosure, a flow regulating device includes a support structure and a mesh element. In some embodiments, the support structure has a proximal end and a distal end, with a lumen defined through the support structure and extending between the proximal end and the distal end. In some embodiments, the mesh element is positioned and sized and configured to control flow of materials through the lumen through the support structure.

In some embodiments, the support structure includes a proximal retention member at the proximal end thereof sized to inhibit migration of the flow-regulating device through the body passage; and the mesh element is coupled to the proximal retention member. In some embodiments, the proximal retention member is formed of a first proximal wall adjacent the proximal end of the tubular element and a second proximal wall distally spaced from the first proximal wall in a direction towards the distal end of the tubular element. In some embodiments, the mesh element is positioned and held between the first proximal wall and the second proximal wall of the proximal retention member of the tubular element.

In some embodiments, at least one fastener may be provided along a periphery of the mesh element. In some embodiments, the at least one fastener is selected from the group including of loops, clips, barbs, and hooks. In some embodiments, the at least one fastener includes a plurality of loops about a periphery of the mesh element and a plurality of clips extendable through the loops and attachable to the support structure to couple the mesh element to the support structure. In some embodiments, the at least one fastener is formed separately from the mesh element. In some embodiments, the at least one fastener is applied to the periphery of the mesh element and to one of the proximal end or the distal end of the support structure to mount the mesh element with respect to the support structure. In some embodiments, the at least one fastener includes a plurality of fasteners selected from the group including of clips, barbs, and hooks, the fasteners extending across the periphery of the mesh element and about a periphery of the one of the proximal end or the distal end of the support structure. In some embodiments, the plurality of fasteners includes barbs or hooks which are flexible to facilitate removal from the mesh element and the support structure to remove the mesh element from the support structure. In some embodiments, the plurality of fasteners are provided on a base separately formed from the mesh element and the support structure and selectively positionable over a periphery of the mesh element and the support structure to couple the mesh element and the support structure and removable to permit removal of the mesh element from the support structure.

In some embodiments, the mesh element is a first mesh element having a first mesh gauge, the device further including a second mesh element having a second mesh gauge different from the first mesh gauge, the first mesh element being removable from the support structure and replaceable with the second mesh element to alter the flow of materials through the device and through the body passage.

In accordance with another aspect of the present disclosure, a flow-regulating device includes a mesh element having a perimeter; and a plurality of fasteners coupled about the perimeter of the mesh element and configured to engage tissue adjacent or surrounding the body passage; the opening through the mesh element being determinative of the flow of material through the body passage.

In some embodiments, the mesh element is curved to be secured within an anatomical structure upstream of the body passage with at least a periphery of the mesh element lying against the wall of the anatomical support structure. In some embodiments, the mesh element is curved to fit within a stomach proximal to the pylorus, flow of material passing through the mesh element and to the pylorus being unimpeded. In some embodiments, at least a portion of the mesh element lies against the wall of an anatomical structure and is uncoated to allow tissue ingrowth into the mesh element.

In accordance with various principles of the present disclosure, method of controlling flow of material through a pylorus includes inserting a support structure through the pylorus; and coupling a mesh element to the support structure, the mesh element having a mesh gauge dimensioned to control flow of materials through the support structure.

In some embodiments, the mesh element is exchanged with a different mesh element having a different mesh gauge.

In some embodiments, the method further includes inserting the support structure through the pylorus before coupling the mesh element to the support structure; allowing the support structure to anchor within the pylorus; allowing material to flow through a lumen defined through the support structure; and coupling the mesh element to the support structure after the support structure has been anchored within the pylorus to control flow of materials through the support structure lumen and thereby to control flow of materials through the pylorus.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 7 illustrates a cross-sectional view of an embodiment of a flow-regulating device formed in accordance with various principles of the present disclosure and positioned in a schematic representation of a gastrointestinal environment.

DETAILED DESCRIPTION

Figure 1:
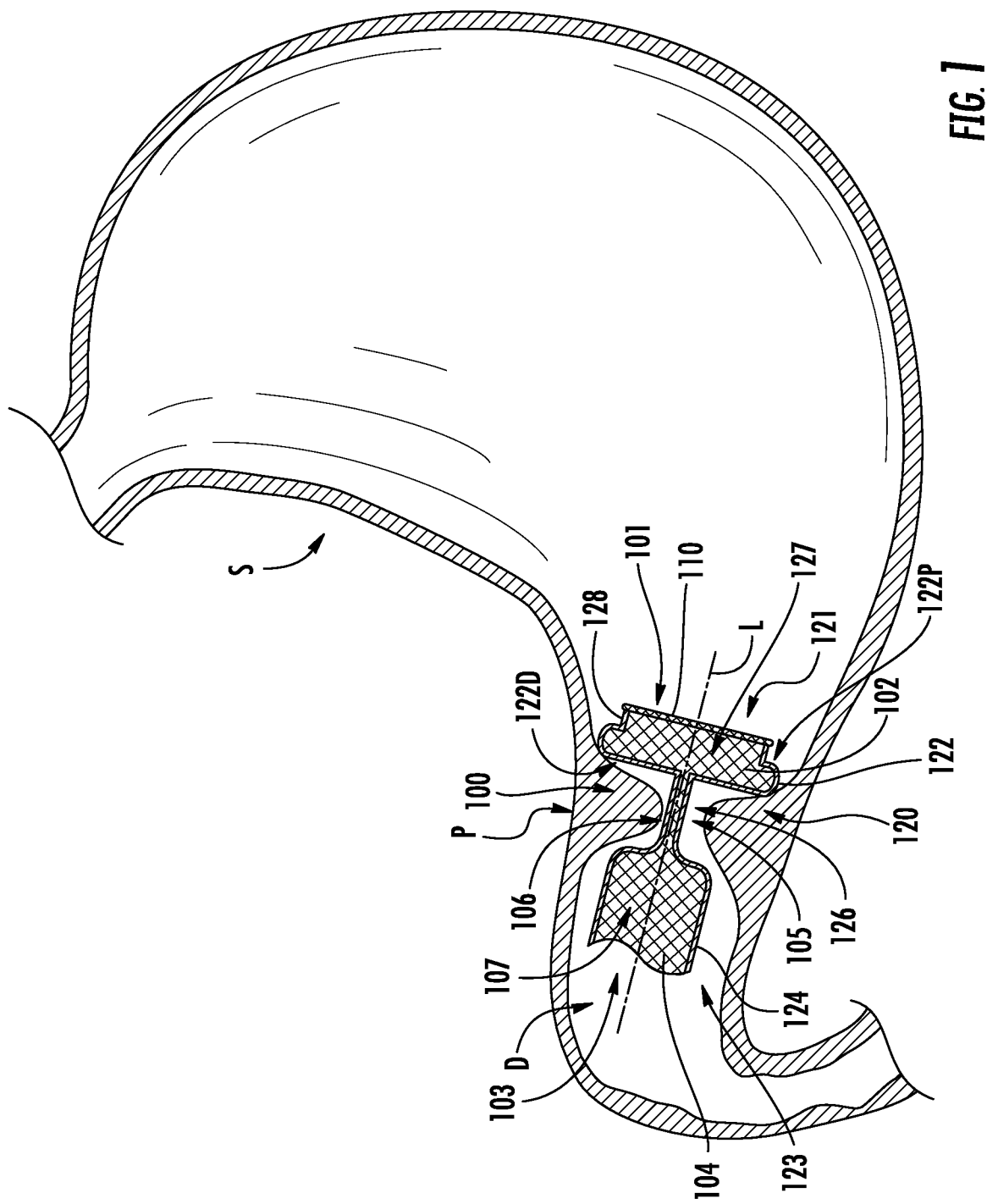
FIG. 1 illustrates an elevational view of an embodiment of a flow-regulating device formed in accordance with various aspects of the present disclosure and positioned in a schematic representation of a gastrointestinal environment.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). The terms "upstream" and "downstream" may be used to refer to the environment in which a device disclosed herein is used (e.g., flow of materials having an upstream direction and a downstream direction), and to describe elements, features, movements, etc., relative to such environment. "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various broad principles of the present disclosure, an implantable device for regulating flow through an anatomical structure includes a mesh element. It will be appreciated that the term anatomical structure may be used interchangeably herein with terms such as body passage or lumen or cavity or the like without intent to limit. The mesh element is used to regulate the flow of materials through a body passage, such as to effect restriction of flow through or closure of the body passage. The mesh element may be formed of any web, net, screen, weave, knit, etc. of filaments or fibers (e.g., metal, polymer, etc.) in any degree of tightness forming a network through which the flow of a material (e.g., chyme) may be regulated (e.g., the rate of material flow slowed). The mesh gauge (generally, a measurement of the size, distribution, shape, etc., of openings through the mesh element) may be selected depending on the materials to be blocked from passing therethrough. In some embodiments, the mesh element is formed of a layer of woven or interwoven or knitted filaments or fibers such that the thickness of the mesh element is significantly less than its length/width dimension. The mesh element may be configured to be self-supporting so that it maintains a given shape independently of other structures or devices (which may facilitate delivery and deployment thereof as will be appreciated), such as once deployed. Preferably, the mesh element is sufficiently resistant to flexing or bending or collapsing, at least once deployed, to withstand pressures induced by the flow of materials against the mesh element which are too large to pass through the mesh element as well as shear forces induced by materials passing through the mesh element.

In some embodiments, the mesh element may be delivered in a compact configuration and may be expanded at the deployment site. For instance, the mesh element may be collapsed or folded or rolled into a relatively compact configuration for transluminal delivery to the treatment site (e.g., a body passage through which flow is to be regulated). The mesh element may be formed to be self-expanding (e.g., formed of a shape memory material to expand independently of another structure or device), such as once deployed. It will be appreciated that the deployment site is generally to be understood as the intended treatment site or position of the device once deployed (e.g., location where the device is implanted) and in use. During the course of treatment, the mesh element may be exchanged with another mesh element having a different mesh gauge to adjust flow of material through the passage to be regulated by the mesh element.

In some embodiments, the flow-regulating device includes a separate support structure or scaffold for the mesh element. The separate support structure may be a tubular element such as a stent or other structure or device known in the art and configured to extend through a body passage. The tubular element may have a lumen defined therethrough configured to regulate or occlude (partially or totally) flow of material through a body passage, or may allow relatively unimpeded flow of material therethrough. Generally, the support structure is formed to be self-supporting such that the support structure maintains a given shape independently of other structures or devices. In some embodiments, the tubular element may be considered to form a scaffold structure on which the mesh element may be held in place with respect to the body passage to be affected by the mesh element. The mesh element may be formed separately from the tubular element and coupled thereto to allow for the desired flow-regulating characteristics of the mesh element to be achieved without affecting the nature of the tubular element, such as which may otherwise affect the structural integrity of the tubular element. It will be appreciated that terms such as coupled (and conjugations thereof) may be used interchangeably herein with terms such as mounted or anchored or attached or secured or engaged or held or the like without intent to limit. The support structure or scaffold may be positioned with respect to the body passage (e.g., with a portion extending through the body passage) to be secured with respect to the body passage (e.g., implanted therein). Such support structure or scaffold may be deployed or implanted during a separate procedure before the mesh element is deployed to allow time for secure implantation (e.g., as a result of tissue ingrowth therein).

Any appropriate known or heretofore known form of a support structure may be used as one of ordinary skill in the art would appreciate. For instance, the support structure may be formed from a plurality of strands or wires or filaments which may be braided or woven or twisted or wrapped or intertwined or knitted or looped (e.g., bobbinet-style) or knotted or otherwise formed into a self-supporting structure. Alternatively, the support structure may be formed from a laser-cut tube or bonded elongated elements or another self-supporting structure. In some embodiments, the support structure may be an expandable stent having a retention member or flange along one or both ends to inhibit migration of the stent with respect to the anatomical structure at which the stent is deployed. A saddle may be defined between the ends of the stent and configured to be deployed through a body passage. A lumen may be formed through the stent, through the flange(s) and the saddle. The flange may extend transverse to the longitudinal axis of the stent (along which the saddle extends along a body passage through which flow is to be regulated), and the mesh element may be mounted on the stent via the flange. In accordance with various principles of the present disclosure, a flange may be provided along the upstream end of the stent. The mesh element may be mounted on such flange, such as across an opening in such flange in fluid communication with the lumen through the stent to regulate flow of materials therethrough.

In some embodiments, the flange wall includes a generally longitudinally extending lip (e.g., surrounding the opening in the flange), and the mesh element is mounted on the lip. In some embodiments, a double-walled flange is provided along an end of the stent. The double-walled flange has an inner wall, adjacent to and facing the saddle, spaced from an outer wall facing away from the saddle. The stent lumen may extend through the double-walled flange and through an opening in the outer wall to allow access to the space between the walls for deployment of a mesh element therein. It will be appreciated that the size of a lumen or any opening in a flange of a support member and/or lip extending from a flange of a support member may be varied to suit the particular needs and functions of the flow-regulating device as may be appreciated by those of ordinary skill in the art.

The adjustable tubular device may be formed of a biocompatible metal or a polymeric material or an alloy. It will be appreciated that in some embodiments it is beneficial for such support structure to be movable or shiftable from a compact collapsed configuration and an expanded configuration. The support structure may be self-expanding once unsheathed from or otherwise no longer held (e.g., constrained) within a delivery device, or may be expanded with the assistance of another expandable device, such as an expandable balloon. For instance, the support structure may be formed of a shape memory material which expands the device once no longer held or constrained within a delivery device.

In embodiments in which a mesh element is provided on an independent (e.g., separately formed) support structure, modifications to the flow of materials through the device may be more readily controlled by customizing the mesh element rather than modifying the structure of the support structure. In prior flow-regulating devices, various properties of the walls of the device (shape, size, configuration, permeability through the wall itself, etc.) had been modified to adjust flow of materials through the device. If it is desired to adjust/modify the rate of flow of materials through a body passage, a mesh element in accordance with various principles of the present disclosure may be more readily adjusted (such as by removal and/or replacement) than prior flow-regulating devices which have been generally larger (and thus may present further challenges than a smaller device such as a mesh element as described herein may present) and/or which may become adhered to the deployment site, such as a result of tissue ingrowth. For instance, instead of optimizing features of the support structure to regulate flow of materials therethrough, the support structure may be optimized for anchoring or stabilizing the flow-regulating device, and the mesh element may be optimized for the desired flow regulation properties.

A mesh element formed in accordance with various principles of the present disclosure may be coupled to a support structure and deployed therewith. Alternatively, the support structure may be positioned within or through a body passage in advance of placement of the mesh element to allow for stabilization of the support structure (e.g., for the support structure to be secured against migration) with respect to the deployment site prior to placement of the mesh element. More particularly, the support structure may be deployed in advance of deployment of the mesh element to allow for tissue ingrowth into the support structure or otherwise to allow for stabilization to be assured with respect to the body passage before the mesh element is deployed. In some embodiments, the support structure includes structures or features to promote stabilization, such as by tissue ingrowth (e.g., into uncoated regions of the support structure). In such embodiment, the mesh element need not be directly mounted with respect to the tissue surrounding or adjacent the body passage.

In accordance with one aspect of the present disclosure, the mesh element may be removably coupled with the support structure. As such, during the course of treatment, if it is desired and/or medically indicated to adjust the rate of flow of material through the mesh element, the mesh element may be removed and exchanged/replaced (such terms, and conjugations thereof, may be used interchangeably herein without intent to limit) with a mesh element having different properties, such as a different mesh gauge. It will be appreciated that terms such as exchanged and replaced (and conjugations thereof) may be used interchangeably herein without intent to limit unless otherwise indicated.

Various forms of fasteners may be used to couple or otherwise hold in place the mesh element with respect to the tubular element, such as sutures, clips, hooks, retaining bands, and other appropriate fasteners known or heretofore known in the art, the specific details of which are not critical to the broad principles of the present disclosure. Any desired number of fasteners or combinations of fasteners may be used. In some embodiments, the mesh element may be provided with loops or eyelets to facilitate coupling of a fastener thereto as well as to the support structure. The fastener may be formed as a part of or separately formed from and carried on one or both of the mesh element and the support structure, or may be separately formed and applied or otherwise coupled to the mesh element and the support structure. The fasteners used to couple a replacement mesh element to the support structure (which may remain in place at the deployment site without being removed for exchange thereof) may be the same or different in structure and/or number from the fasteners initially used. In some embodiments, the fasteners are resilient to securely couple the mesh element and the support structure, yet to allow disengagement of the mesh element from the support structure if desired or medically indicated, such as to be exchanged or replaced with another mesh element, or even to be removed entirely.

The particular shape of the mesh element may be selected in view of the manner in which the mesh element is to be deployed. For instance, if the mesh element is to be coupled to a support structure with a generally circular cross-sectional shape, then the mesh element may be in the general shape of a disk. A disk-shaped mesh element may be substantially planar (e.g., substantially flat) or curved or conical or otherwise nonplanar to engage a support structure or otherwise be securely mounted to (e.g., to fit within) a body cavity or opening into a body passage. The mesh element may be formed of a shape memory material to retain a desired shape such as a curved or nonplanar shape. As such, the mesh element may be delivered in a collapsed, compact configuration to be delivered transluminally or endoscopically (i.e., through a natural body passage or orifice without the need for open surgery), and may expand (e.g., self-expand) to the desired deployed configuration.

In some embodiments, the mesh element may be directly anchored to tissue adjacent or surrounding the body passage through which material flow is to be regulated by the mesh element, without the use of another mounting or deployment structure such as the above-described support structure. In such embodiments, the fasteners which may be used with the mesh element may be in the form of tissue-engaging elements configured to directly couple or anchor to tissue surrounding or adjacent the body passage through which material flow is to be regulated. The tissue to which the mesh element is implanted (e.g., coupled, mounted, etc.) may be pre-treated in any known or heretofore manner (e.g., cauterization, argon plasma coagulation, etc.) and/or the mesh element may be configured (e.g., uncoated) to promote tissue ingrowth. The shape and/or configuration of the mesh element may be determined based on the shape and/or configuration of the deployment site (e.g., the anatomical structure to which the mesh element is coupled or anchored). For instance, it may be desirable for the mesh element to be cup-like or conical or otherwise to present a concave side and a convex side. Generally, the concave side faces upstream, and the convex side faces the body passage through which flow is to be regulated by the mesh element. However, other configurations are within the scope and spirit of the present disclosure. In some embodiments, the periphery of the mesh element may be laid against the body tissue with respect to which the mesh element is to be implanted to increase the surface area of contact by mesh element for enhanced securement and reduced likelihood of migration. An increased contact area may distribute holding forces over a larger surface area, thereby reducing the amount of force needed to secure the device at a given point. Nonetheless, the surface area of contact of such mesh element with body tissue may still generally be smaller than the surface area contacted by prior flow-regulating devices to better facilitate removal if desired. In some embodiments, the mesh element is the only flow-regulating element of a flow-regulating device formed in accordance with principles of the present disclosure, and thus may be considered to be determinative of the flow of material through the body passage. In other words, materials may flow from one (upstream) face of the mesh element, through the openings within the mesh element, and out the opposite (downstream) face of the mesh element and directly into the body passage through which material flow is being regulated without being further regulated by another flow-regulating device, thereby simplifying assembly, delivery, and functioning of a flow-regulating device formed in accordance with various principles of the present disclosure.

In accordance with one aspect of the present disclosure, a flow-regulating device formed in accordance with various principles of the present disclosure may be used in the treatment of various metabolic disorders. For instance, a flow-regulating device formed in accordance with various principles of the present disclosure may be used to regulate (as used herein, to control or prevent or otherwise affect) the flow of materials (e.g., food, chyme, fluid, etc.) from the stomach into the small intestines. More particularly, a flow-regulating device formed in accordance with various principles of the present disclosure may be used to regulate the flow of materials from the stomach through the pylorus and into the duodenum. Such regulation of flow of materials through the pylorus may be desirable in a gastric bypass or in bariatric treatments involving regulation of gastric emptying. One or more mesh elements may be supplied in various gauges to act as a filter for the allowable passage of gastric materials therethrough and thus through the pylorus. For instance, a first mesh gauge may occlude 90-95% of gastric materials, and a second mesh gauge may occlude 80-85% of gastric materials. The different mesh elements may be deployed in a sequence as indicated by the course of treatment prescribed for the patient, and/or in view of the patient's progress with the mesh element that has been deployed. As various disorders (e.g., diabetes, nonalcoholic steatohepatitis, obesity, or other gastrointestinal diseases or disorders) may require different courses of treatment, and differing extents to which gastric flow is occluded or regulated (e.g., passage thereof slowed), interchangeability of mesh elements may be a particularly beneficial feature of a flow-regulating device formed in accordance with the present disclosure.

Various embodiments of flow-regulating devices will now be described with reference to examples illustrated in the accompanying drawings. Reference in this specification to "one embodiment," "an embodiment," "some embodiments", "other embodiments", etc., indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/ or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

In the accompanying drawings, it will be appreciated that elements or components similar among the various illustrated embodiments are generally designated with the same reference numbers increased by 100 and redundant description is omitted. Common features are identified by common reference elements and, for the sake of brevity, the descriptions of the common features are generally not repeated. Certain features in one embodiment may be used across different embodiments and are not necessarily individually labeled when appearing in different embodiments. For purposes of clarity, not all components having the same reference number are numbered.

Turning now to the drawings, an example of an embodiment of an implantable flow-regulating device 100 formed in accordance with various principles of the present disclosure is illustrated as deployed in a schematic representation of a gastrointestinal environment, although other uses and/or environments are within the scope and spirit of the present disclosure. The illustrated flow-regulating device 100 has a first end 101, which may be referenced herein as a proximal end 101 (without intent to limit), and a second end 103, which may be referenced herein as a distal end 103 (without intent to limit), with an intermediate region 105 extending therebetween. In the example of an environment illustrated in FIG. 1, the intermediate region 105 of the flow-regulating device 100 is deployed across a pylorus P with the distal end 103 (generally deployed first, and thus referenced herein as distal for the sake of convenience and without intent to limit) positioned within the duodenum D, and the proximal end 101 (generally deployed last, and thus referenced herein as proximal for the sake of convenience and without intent to limit) positioned within the stomach S. Materials (e.g., fluid, chyme, etc.) may flow through a lumen 107 defined through the flow-regulating device 100 in a direction from the proximal end 101 (upstream) to the distal end 103 (downstream) of the flow-regulating device 100. The flow-regulating device 100 may include retention members 102, 104 shaped and configured to retain the flow-regulating device 100 in the deployed position and to resist or inhibit or prevent migration (e.g., through the pylorus P distally into the duodenum D or proximally into the stomach S). In the illustrated embodiment, a proximal retention member 102 is provided along the proximal end 101 of the flow-regulating device 100, and a distal retention member 104 is provided along the distal end 103 of the flow-regulating device 100. Although the proximal retention member 102 is illustrated as having a generally circular/disk shape, and the distal retention member 104 is illustrated as having a more elongated/cylindrical shape, other configurations capable of facilitating retention of the flow-regulating device 100 in the deployed position are within the scope and spirit of the present disclosure. The retention members may be formed of a single wall or two spaced-apart walls (i.e., forming a double-walled retention member). A narrower region, such as a saddle 106, may be defined or provided between the proximal retention member 102 and the distal retention member 104 to fit through the body passage through which flow is to be regulated by the flow-regulating device 100—in the illustrated example, a pylorus P.

The example of an embodiment of a flow-regulating device 100 illustrated in FIG. 1 includes a mesh element 110 and a support structure 120. The support structure 120 of the embodiment illustrated in FIG. 1 is a substantially tubular element and has a lumen 127 defined therethrough, allowing materials (such as gastric materials) to flow therethrough. The mesh element 110 extends across the lumen 127 to regulate flow therethrough. As illustrated in the example of FIG. 1, the mesh element 110 is provided along the proximal end 101 of the flow-regulating device 100, although other positions are within the scope and spirit of the present disclosure. As used herein, the term provided (and other grammatical forms and conjugations thereof) generally includes mounted, coupled, engaged with, extended, positioned, etc. (and other grammatical forms and conjugations thereof) unless otherwise indicated, and such terms may be used interchangeably herein without intent to limit. One or more fasteners may be used to couple the mesh element 110 with the support structure 120, as described in further detail below.

In the embodiment illustrated in FIG. 1, the proximal retention member 102 of the flow-regulating device 100 may be formed along the proximal end 121 of the support structure 120 as a proximal flange 122, and the distal retention member 104 of the flow-regulating device 100 may be formed along the distal end 123 of the support structure 120. The intermediate region 105 between the proximal end 101 and the distal end 103 may be configured as a saddle 126. In some embodiments, the proximal flange 122 is substantially disk-shaped, with a longitudinal extent along the longitudinal axis L of the flow-regulating device 100 generally shorter than a dimension in the cross-sectional direction transverse to the longitudinal axis L. For instance, in some embodiments, the ratio of the cross-directional dimension to the longitudinal dimension may be as large as approximately 10:1, but may be as small as approximately 3:1 and even as small as approximately 2:1, including increments of 0.25:1 therebetween. The mesh element 110 of the example of an embodiment illustrated in FIG. 1 may be provided along the proximal flange 122 of the support structure 120, although other positions are within the scope and spirit of the present disclosure. The proximal flange 122 may be positioned upstream of a flow to be regulated by the flow-regulating device 100, with the distal flange 124 downstream of such flow. In some embodiments, at least the proximal flange 122 is a double-walled flange with an outer/proximal flange wall 122P (along which the mesh element 110 may be extended) and an inner/distal flange wall 122D (adjacent/facing the saddle 126) spaced apart from each other. The proximal flange 122 may include a longitudinally extending lip 128 (extending proximally from the proximal flange wall 122P in the example of an embodiment illustrated in FIG. 1) to which the mesh element 110 may be coupled, as described in further detail below. Additionally or alternatively, in some embodiments, the distal flange 124 may be more elongated than the proximal flange 122 along the longitudinal axis L of the flow-regulating device 100. In some embodiments, at least a portion of the support structure 120 (such as tissue-facing surfaces of the support structure 120, such as the faces of the proximal flange 122 and the distal flange 124 facing inwardly towards the saddle 126) may be uncoated to promote tissue growth therein/thereto. It will, however, be appreciated that other configurations of the proximal flange 122 and the distal flange 124 are within the scope and spirit of the present disclosure.

In some embodiments, the mesh element 110 extends over the open proximal end 121 of the support structure 120 (e.g., an opening through proximal flange 122) so that materials must pass through the mesh element 110 prior to passing through the lumen 127 of the support structure 120. The mesh element 110 has a mesh gauge configured to regulate the rate of flow of materials through the mesh element 110, and thereby to regulate the materials which flow through the flow-regulating device 100 via the lumen 127 of the support structure 120. In view of the structure of the mesh element 110 of the flow-regulating device 100, the intermediate region 105 of the flow-regulating device 100 need not be narrowed relative to the proximal end 101 and the distal end 103 of the flow-regulating device 100 (such as illustrated) and may be configured to allow substantially unimpeded flow therethrough, with the mesh element 110 regulating the flow of materials through the flow-regulating device 100. For instance, in the example of an embodiment illustrated in FIG. 1, the intermediate region 105 may be a region of the support structure 120, and may be referenced herein as a saddle 126, although other configurations are within the scope and spirit of the present disclosure. Although in prior flow-regulating devices the lumen of a similar saddle may be narrowed or constricted to regulate flow of materials through the device, in the illustrated embodiment having a mesh element 110 in accordance with various principles of the present disclosure, the portion of the lumen 127 through the saddle 126 of the support structure 120 need not be narrowed or constricted. In some embodiments, the saddle 126 may minimally affect the flow of materials through the flow-regulating device 100, with the flow regulation being controlled primarily by the mesh element 110. As such, modifications to the flow of materials may be more readily controlled by customizing a mesh element 110 rather than modifying the structure of the support structure 120.

The mesh element 110 may be coupled to or otherwise engaged with the support structure 120 in any of a variety of manners. Preferably, such coupling or engagement is sufficiently secure to withstand the pressures against the mesh element 110 caused by peristaltic movement and/or gastric materials flowing against and through the mesh element 110 (which may be influenced by how full the stomach is and/or the individual patient and/or the mesh size/gauge). In some embodiments, one or more fasteners are provided, either as integral parts of the mesh element 110 and/or the support structure 120, or as separate elements coupled or engaged thereto. Various embodiments of fasteners are illustrated in the accompanying figures as nonlimiting illustrative examples, as will now be described.

Figure 2:
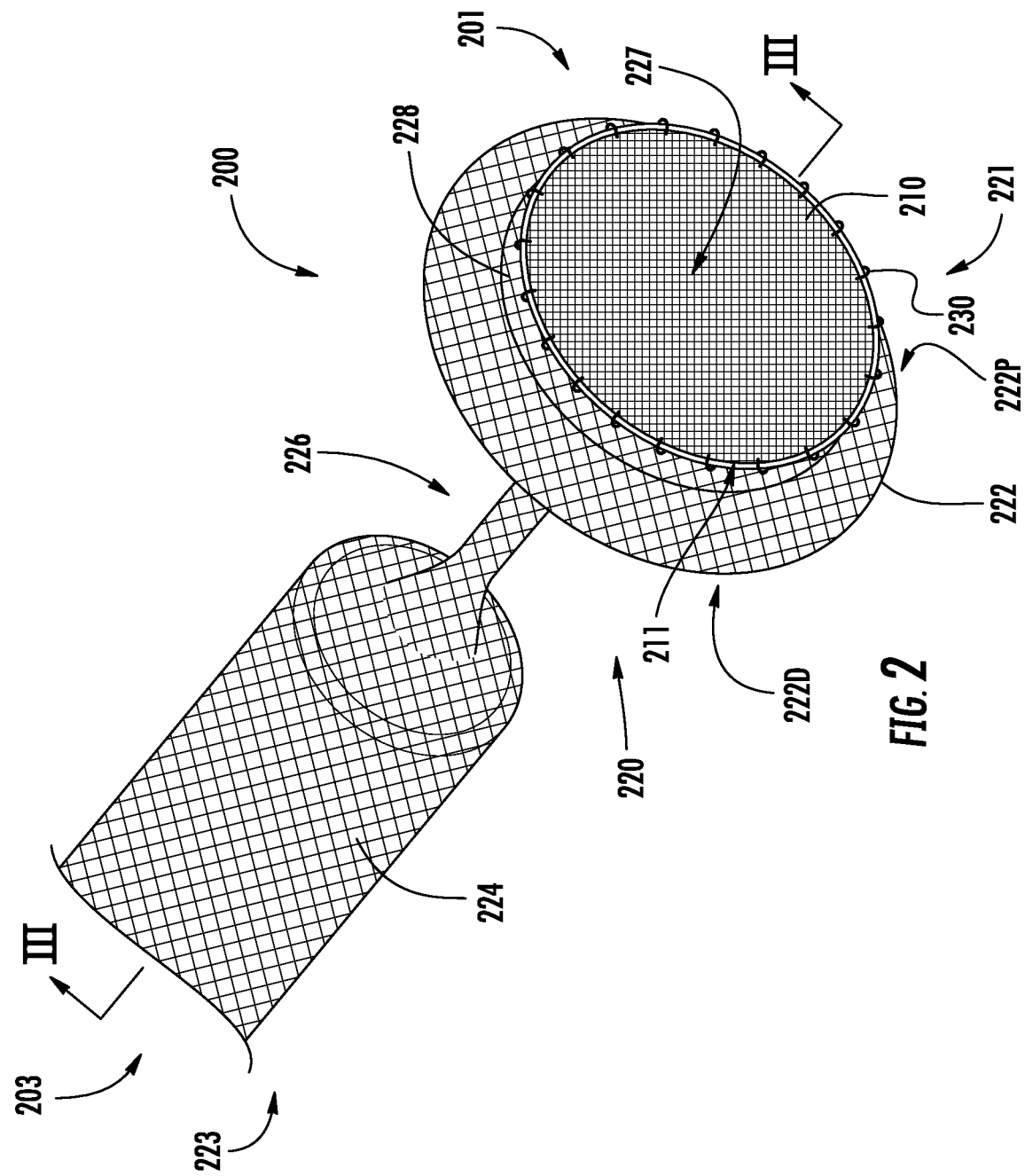
FIG. 2 illustrates a proximal perspective view of an example of an embodiment of a flow-regulating device formed in accordance with various principles of the present disclosure.

In the example of a flow-regulating devices 200 illustrated in FIG. 2, a mesh element 210 is coupled to a proximal end 221 of a support structure 220. In the illustrated embodiment, the support structure 220 is a substantially tubular element with a lumen 227 extending therethrough, and the mesh element 210 is extended across the opening to the lumen 227 so that materials passing through the lumen 227 first pass through, and are regulated by (such as by the mesh gauge/size of) the mesh element 210. In the illustrated embodiment, the support structure 220 includes a retention member in the form of a proximal flange 222. The lumen 227 extends through the proximal flange 222, a saddle 226, and an optional distal flange 224. In some embodiments, such as in the illustrated embodiment, the proximal flange 222 includes an extension, such as an axial extension referenced herein as a lip 228. Furthermore, the proximal flange 222 may be a double-walled flange with an inner/distal flange wall 222D adjacent/facing the saddle 226, and an outer/proximal flange wall 222P from which the lip 228 may extend outwardly away from the support structure 220.

The mesh element 210 may be conveniently and/or advantageously coupled to the support structure 220 by being coupled to the lip 228 thereof or other portion of the proximal flange 122. Any of a variety of fasteners may be used to achieve such coupling. The fasteners preferably are configured to couple the mesh element to the support structure to inhibit/prevent migration of the mesh element. It will be appreciated that reference herein to migration is reference to distal and/or proximal migration unless otherwise noted. In the illustrated example, one or more fasteners 230 in the form of hooks are provided to couple the mesh element 210, such as along the periphery 211 thereof, to the support structure 220, such to the proximal flange 222, and, more particularly, such as to the lip 228 thereof. The hooks may be configured to withstand the pressures of materials flowing against and through the mesh element 210 (in either direction), yet may permit removability of the mesh element 210, such as for replacement/interchanging with another mesh element such as with a different mesh gauge. In embodiments in which the mesh element 210 is provided along the proximal end 201 of the flow-regulating device 200 and the one or more fasteners 230 are in the form of hooks, the majority of the concave portion of such hook-shaped fasteners 230 may face distally towards the distal end 203 of the flow-regulating device 200 (at least upon impact of forces on the mesh element 210) to resist distal migration of the mesh element 210 with respect to the support structure 220 in view of the generally stronger distally-directed forces against the mesh element 110. However, it will be appreciated that proximally-directed forces may be encountered by the mesh element 110 as well, and the fasteners 230 should be configured to resist such forces as well.

The hook-shaped fastener 230 illustrated in FIG. 2 may be separately formed from the mesh element 210 and/or the support structure 220, or may be extensions thereof, such as extensions of the periphery 211 of the mesh element 210 or extensions of the lip 228. It will be appreciated that other forms or configurations of fasteners 230 may be used, such as to couple a mesh element 210 to a support structure 220, such as to a proximal end 221, and, more particularly, to a proximal flange 222 of a support structure 220, and, even more particularly, to a lip 228 of a support structure 220, such as illustrated in FIG. 2. For instance, any of a variety of clips (e.g., hemostatic clips such as the RESOLUTION™ Clip sold by Boston Scientific Corporation), sutures, clasps, or other suitable structures known or heretofore known in the art may be used as fasteners 230, the particular configuration not being critical to the scope of the present disclosure.

Figure 3:
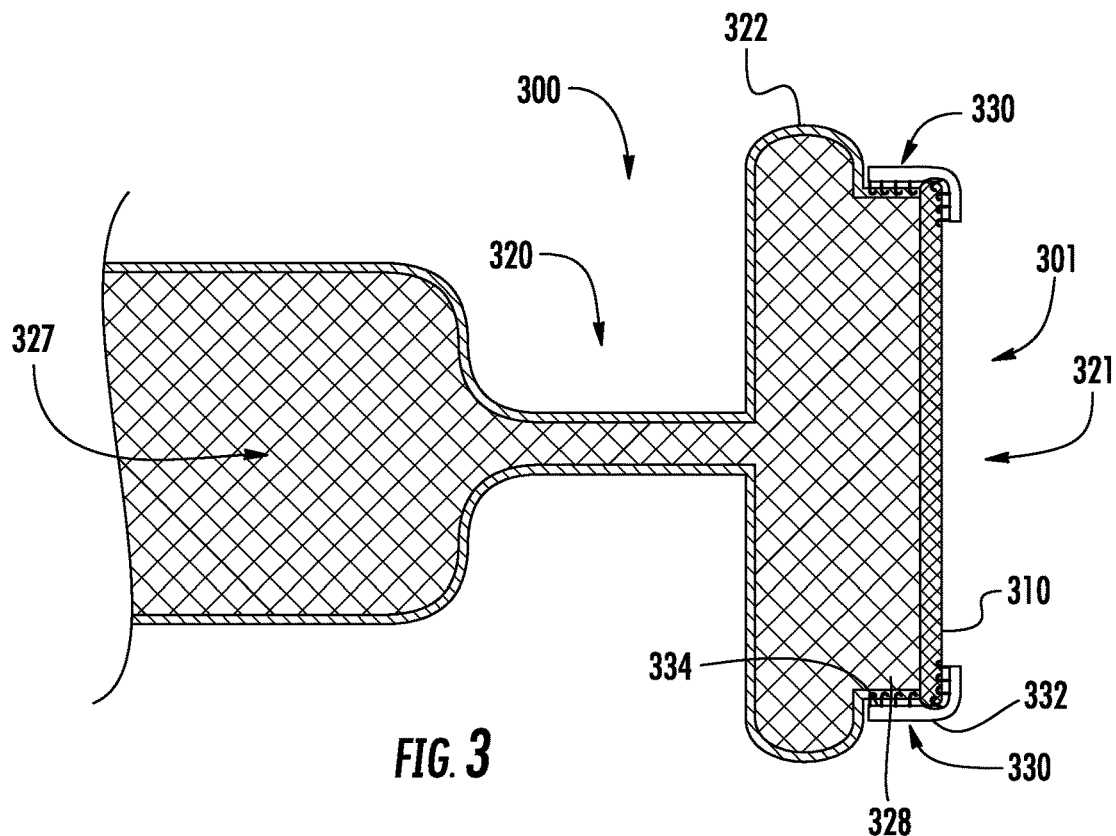
FIG. 3 illustrates a cross-sectional view, such as along a line as illustrated in FIG. 2, of an embodiment of a flow-regulating device formed in accordance with various principles of the present disclosure.

As noted above, a fastener used to couple a mesh element and a support structure in accordance with various principles of the present disclosure may be a separate element applied to or over at least a portion of each of the mesh element and the support structure. For instance, as illustrated in FIG. 3, a fastener 330 in the form of a separately-formed element may be applied over a portion of the mesh element 310 and a portion of the support structure 320 of the illustrated example of an embodiment of a flow-regulating device 300. In some embodiments, the fastener 330 may have a base 332 with one or more engagement elements 334 extending therefrom and configured to engage the mesh element 310 and the support structure 320 to mount the mesh element 310 to the support structure 320, e.g., to the proximal flange 322 of the support structure 320, to regulate flow through the lumen 327 therethrough. The engagement elements 334 may be in the shape of hooks or barbs or anchors or the like, known or heretofore known in the art, configured to securely engage with the mesh element 310 and the support structure 320. For instance, a portion of the engagement element 334 may be inserted between (e.g., in gaps between) the filaments (e.g., wires or fibers) from which the mesh element 310 and/or the support structure 320 is formed (e.g., interwoven or woven or knitted). As noted above with respect to the example of an embodiment of a flow-regulating device 200 illustrated in FIG. 2, the engagement elements 334 may be configured to withstand the pressures of materials flowing against and through the mesh element 310, yet may permit removability of the mesh element 310, such as for replacement/interchanging with another mesh element such as with a different mesh gauge. In some embodiments, in which it may be desirable to remove the mesh element 310 and/or exchange/replace the mesh element 310 with another mesh element 310, the engagement elements 334 are formed to be resilient, such as resiliently biased (and may advantageously be formed from a shape memory material such as Nitinol) to allow disengagement from the mesh element 310 and/or the support structure 320 thereby allowing detachment for removal of the fastener 330. In some embodiments, the fasteners 330 may be a hook and loop material such as known or heretofore known in the art with the desired retention and removability properties.

Figure 4:
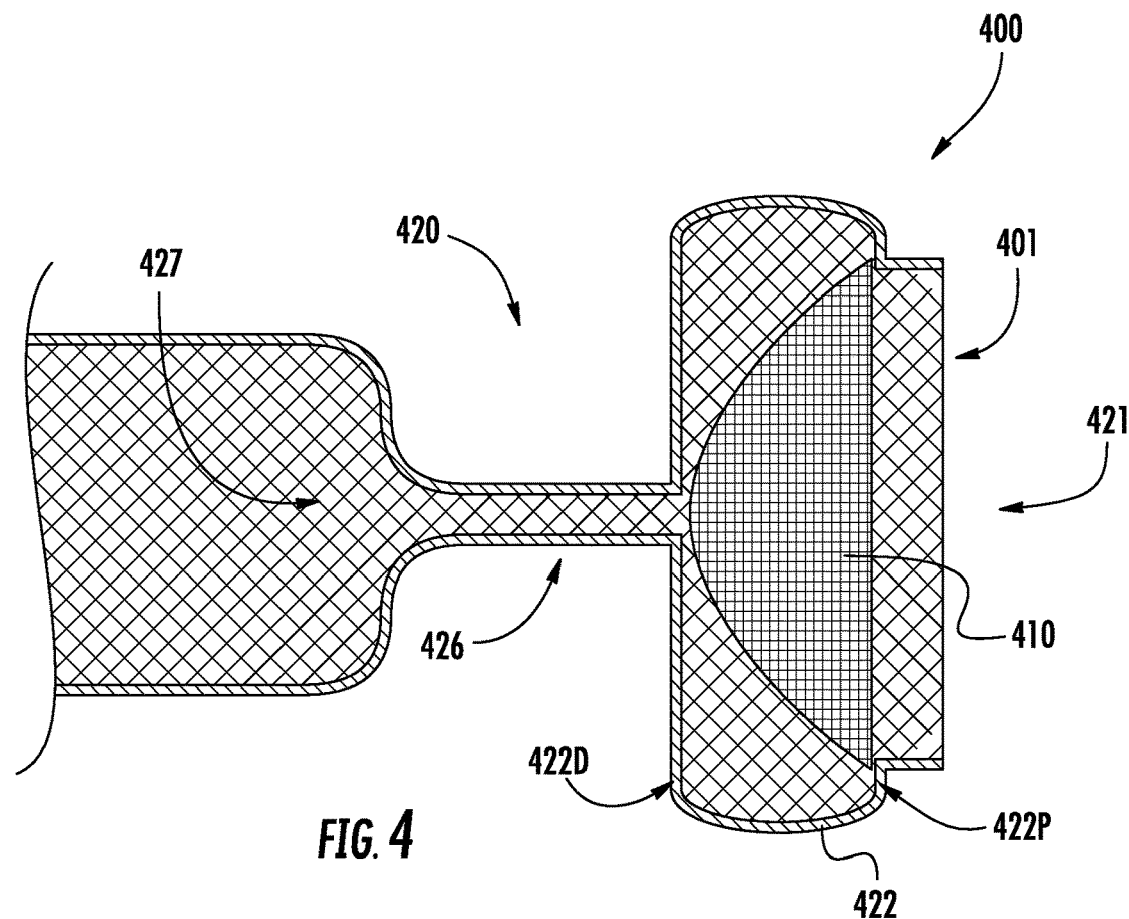
FIG. 4 illustrates a cross-sectional view, such as along a line as illustrated in FIG. 2, of an embodiment of a flow-regulating device formed in accordance with various principles of the present disclosure.

A mesh element formed in accordance with various principles of the present disclosure may be coupled to a proximal end of the support structure and optionally may extend at least partially into a lumen defined within the support structure. In the example of an embodiment of a flow-regulating device 400 illustrated in FIG. 4, a mesh element may be positioned and mounted further within the support structure. For instance, instead of being coupled to a proximally-facing surface of a proximal end of the support structure, such as to a proximally-extending lip of the support structure, a mesh element 410 may be mounted within a lumen 427 of a support structure 420. More particularly, a mesh element 410 may be at least partially retained in place with respect to the support structure 420 (e.g., to inhibit and/or prevent relative migration) by structural features of the support structure 420. In the example of an embodiment of a flow-regulating device 400 illustrated in FIG. 4, the support structure 420 includes a double-wall proximal flange 422 having a proximal flange wall 422P and a distal flange wall 422D distally spaced from the proximal flange wall 422P. The mesh element 410 may be mounted between the proximal flange wall 422P and the distal flange wall 422D. In some embodiments, the mesh element 410 may be delivered in a compact configuration and inserted into the open proximal end 401 of the flow-regulating device 400 to expand and to be held between the proximal flange wall 422P and the distal flange wall 422D. In some embodiments, the mesh element 410 may be self-expandable to shift from a collapsed delivery configuration (e.g., sufficiently compact to be delivered to the flow-regulating device 400 transluminally) to an expanded configuration upon deployment. In the example of an embodiment of a mesh element 410 illustrated in FIG. 4, the mesh element 410 may be concave towards the proximal end 401 of the flow-regulating device 400 to facilitate delivery and removal, as well as to resist proximal migration.

The mesh element 410 and/or the proximal flange wall 422P and/or the distal flange wall 422D of the proximal flange 422 of the support structure 420 may be sufficiently resistant to flexing to provide sufficient holding strength for the mesh element 410 therebetween to prevent migration of the mesh element 410 therefrom. Additionally or alternatively, fasteners such as described above (e.g., a retaining band imparting a force such as resilient/spring force holding the mesh element 410 in place) may be used to ensure secure mounting of the mesh element 410 with respect to the support structure 420 to prevent/inhibit migration of the mesh element 410. The size of the saddle 426, and more particularly the size of the portion of the lumen 427 extending through the saddle 426 may be sufficiently small such that the mesh element 410 cannot migrate distally through the flow-regulating device 400 into the duodenum. The resistance to flexing and/or inversion of the curvature of the flow-regulating device 400 (in the illustrated example, convex in a distal direction and concave in a proximal direction) may be sufficient to inhibit and/or prevent proximal migration of the mesh element 410 out of the space between the proximal flange wall 422P and the distal flange wall 422D. Moreover, flexing of the example of an embodiment of a mesh element 410 illustrated in FIG. 4 would cause the mesh element 410 to splay or spread or otherwise to expand radially outward to be further blocked by the proximal flange wall 422P against proximal migration of the mesh element 410 with respect to the flow-regulating device 400.

Figure 5A:
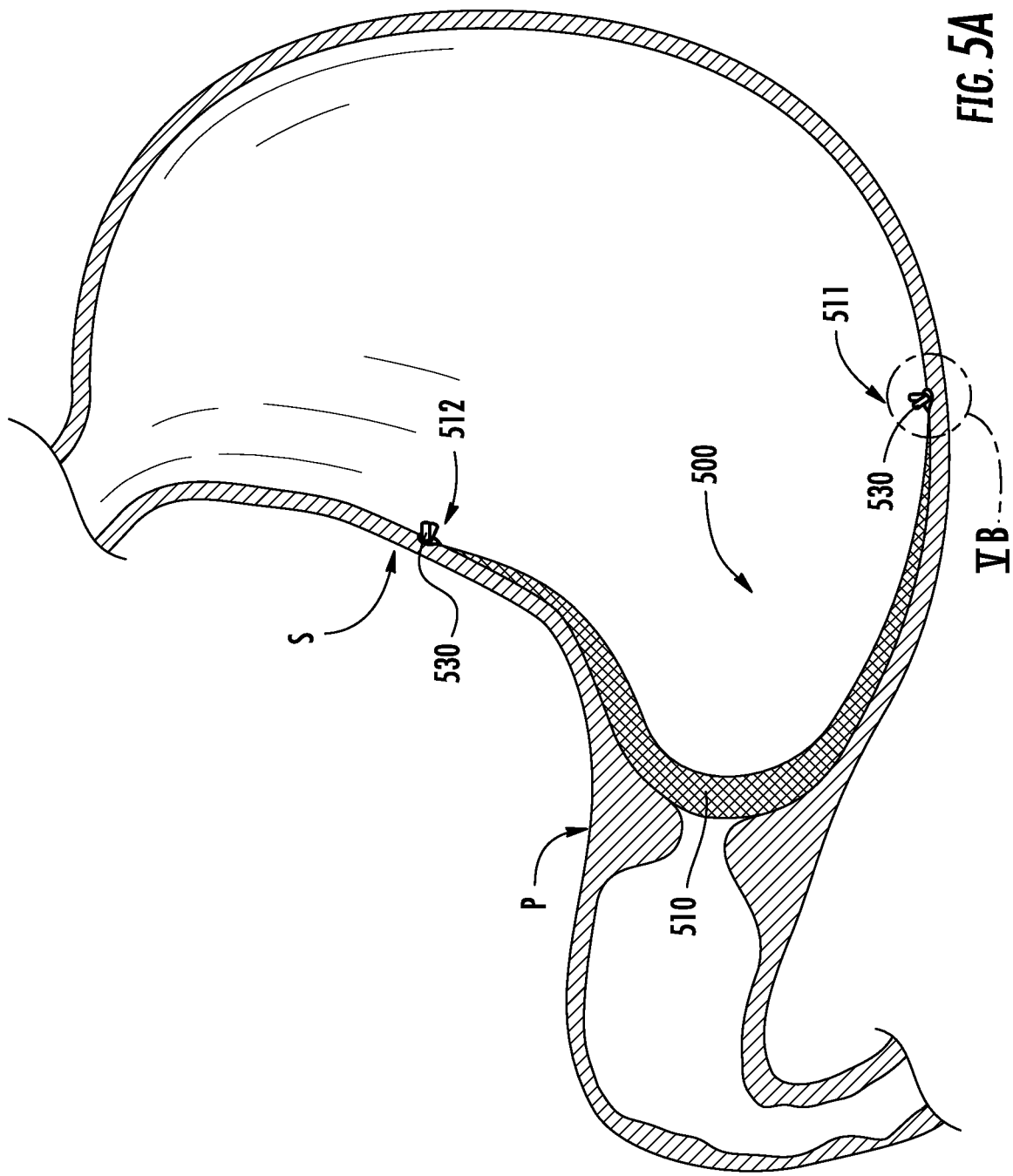
FIG. 5A illustrates a cross-sectional view of an embodiment of a flow-regulating device formed in accordance with various principles of the present disclosure and positioned in a schematic representation of a gastrointestinal environment.
Figure 6A:
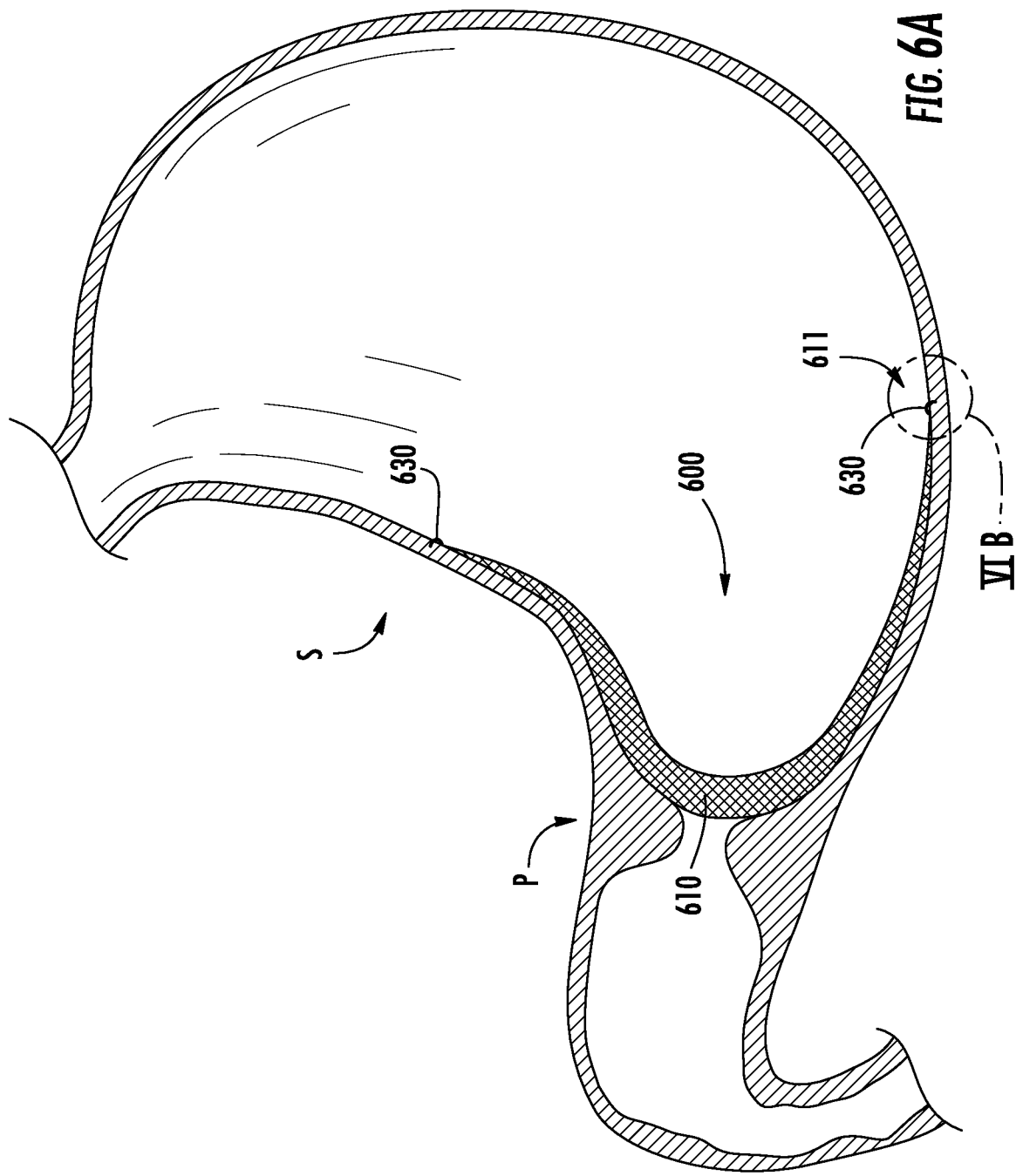
FIG. 6A illustrates a cross-sectional view of an embodiment of a flow-regulating device formed in accordance with various principles of the present disclosure and positioned in a schematic representation of a gastrointestinal environment.

In accordance with various aspects of the present disclosure, a mesh element may be used or deployed independently of a support structure, as in the various examples of embodiments illustrated in FIG. 5A, FIG. 6A, and FIG. 7. For instance, in such embodiments, fasteners which are configured as tissue-engaging elements configured to couple or fix a device to body tissue without damaging the body tissue (various such tissue-engaging elements being known in the art and thus not described in detail herein as such details are not critical to the present disclosure) may be used to anchor the mesh element directly to an anatomical structure without an intervening support structure such as the support structures described above. It will be appreciated that in accordance with such aspects of the present disclosure, flow of materials through the body passage may otherwise be unimpeded by a nonanatomical structure (e.g., separate implanted or deployed device). As such, flow of materials is regulated by a simple mesh element spanning across an anatomical structure (body passage, body cavity, lumen, etc.) upstream of the body passage through which flow of materials is to be regulated. The openings through the mesh element thus may be determinative of the flow of material through the body passage which is otherwise unoccluded by another nonanatomical structure.

Turning to FIG. 5A, a mesh element 510 is illustrated in a schematic representation of a gastrointestinal environment, although other uses and/or environments are within the scope and spirit of the present disclosure. In particular, in the illustrated embodiment, the mesh element 510 is held in place with respect to a stomach S proximal to a pylorus P, however other environments and uses are within the scope and spirit of the present disclosure. An example of a detail view V B of a mesh element 510 such as illustrated in FIG. 5A is illustrated in plan view in FIG. 5B. In the illustrated example, the peripheral shape of the mesh element 510 is generally circular, such as to match or correspond to the generally circular cross-sectional shape of the stomach S. However, it will be appreciated that other shapes, such as in plan view, are within the scope and spirit of the present disclosure.

As may be appreciated from the cross-sectional view of FIG. 5A, the mesh element 510 may have a curved configuration, such as a cupped or conical or paraboloid shape, which need not be fully or even partially symmetrical about a given axis. In some embodiments, as illustrated for example in FIG. 5A, the mesh element 510 is curved or contoured to generally match the contour of the antrum of the stomach S proximal to the pylorus P. Such configuration may allow for greater contact of the mesh element 510 with tissue, with at least a portion (e.g., a portion of the periphery 511) of the mesh element 510 lying against a wall of the anatomical structure (in this example, the stomach S) in which the mesh element 510 is deployed. The mesh openness or density may be constant or varied across the area of the mesh element 510. The mesh element 510 may be partially coated to adjust the openness (such as the total area of openings in the mesh element 510 relative to the total area of the mesh element 510) of the underlying mesh structure (the wires or filaments or the like forming the mesh element 510). However, in some embodiments, a portion of the mesh element 510, such as the periphery 511 thereof, may remain uncoated to promote tissue ingrowth to secure or stabilize the mesh element 510 in place with respect to the tissue at the deployment site to inhibit or prevent migration of the mesh element 510 with respect to the deployment site. A plurality of fasteners 530 may be provided, such as about the periphery 511 of the mesh element 510 to hold the mesh element 510 in place with respect to an anatomical structure. The greater the curvature of the mesh element 510 to include a portion thereof which may be laid or placed along the tissue at the deployment site, the greater the surface area along which the mesh element 510 may be secured, either by separate fasteners 530 or tissue ingrowth.

Figure 5B:
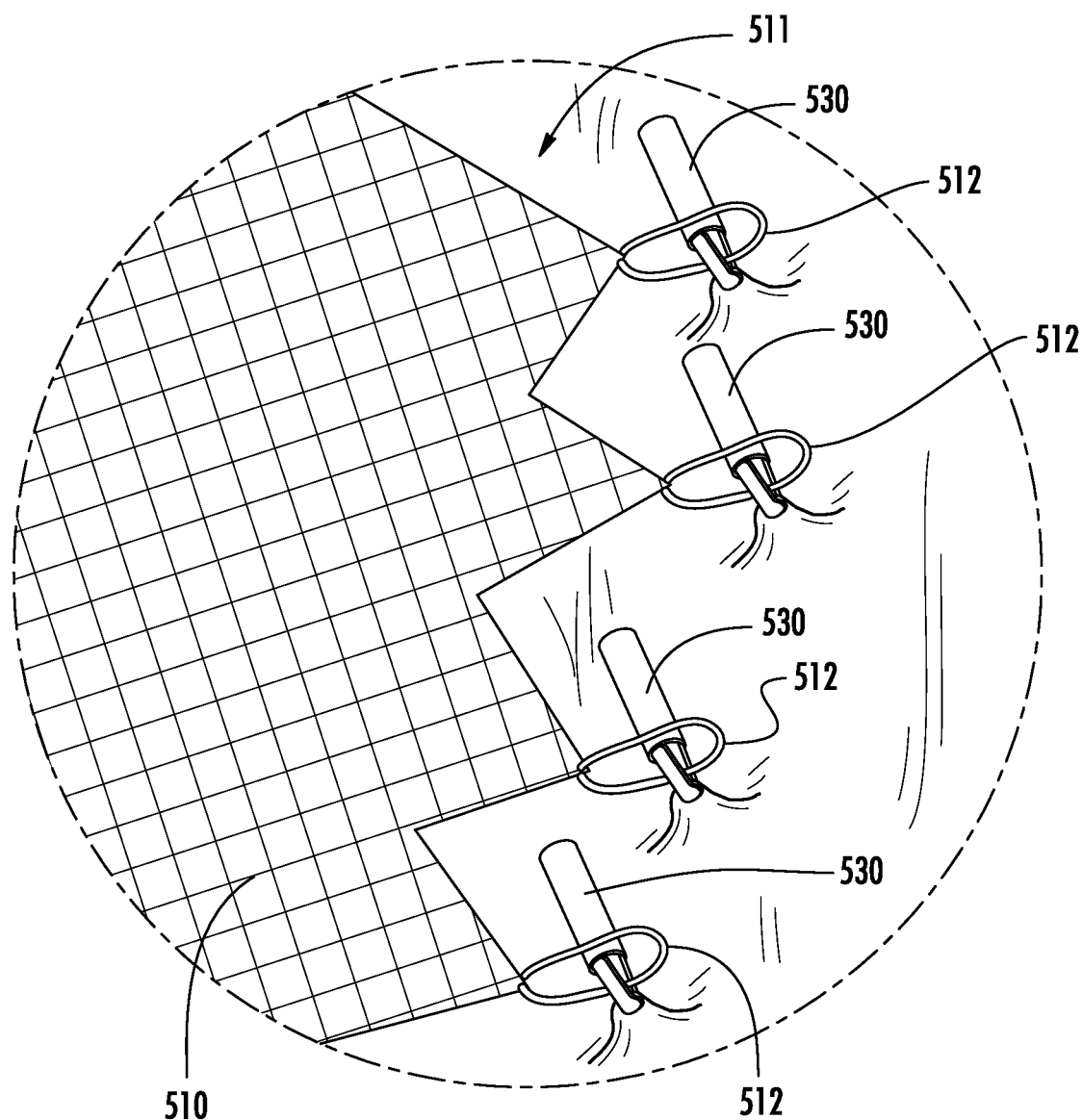
FIG. 5B illustrates a generally plan view of a detail V B of an embodiment of a flow-regulating device as illustrated in FIG. 5A.

In some embodiments, such as may be appreciated with reference to the detail V B of FIG. 5A illustrated in plan view in FIG. 5B, the mesh element 510 includes structures facilitating engagement of fasteners 530 thereto. For instance, one or more loops 512 may be provided about the periphery 511 of the mesh element 510, and at least a portion of one or more of the fasteners 530 may extend through a respective loop 512 to anchor the mesh element 510 to tissue. It will be appreciated that such loops 512 are optional, the fasteners 530 being capable of grasping a mesh element 510 without such loops 512 along with tissue to anchor the mesh element 510 to the tissue.

Figure 6B:
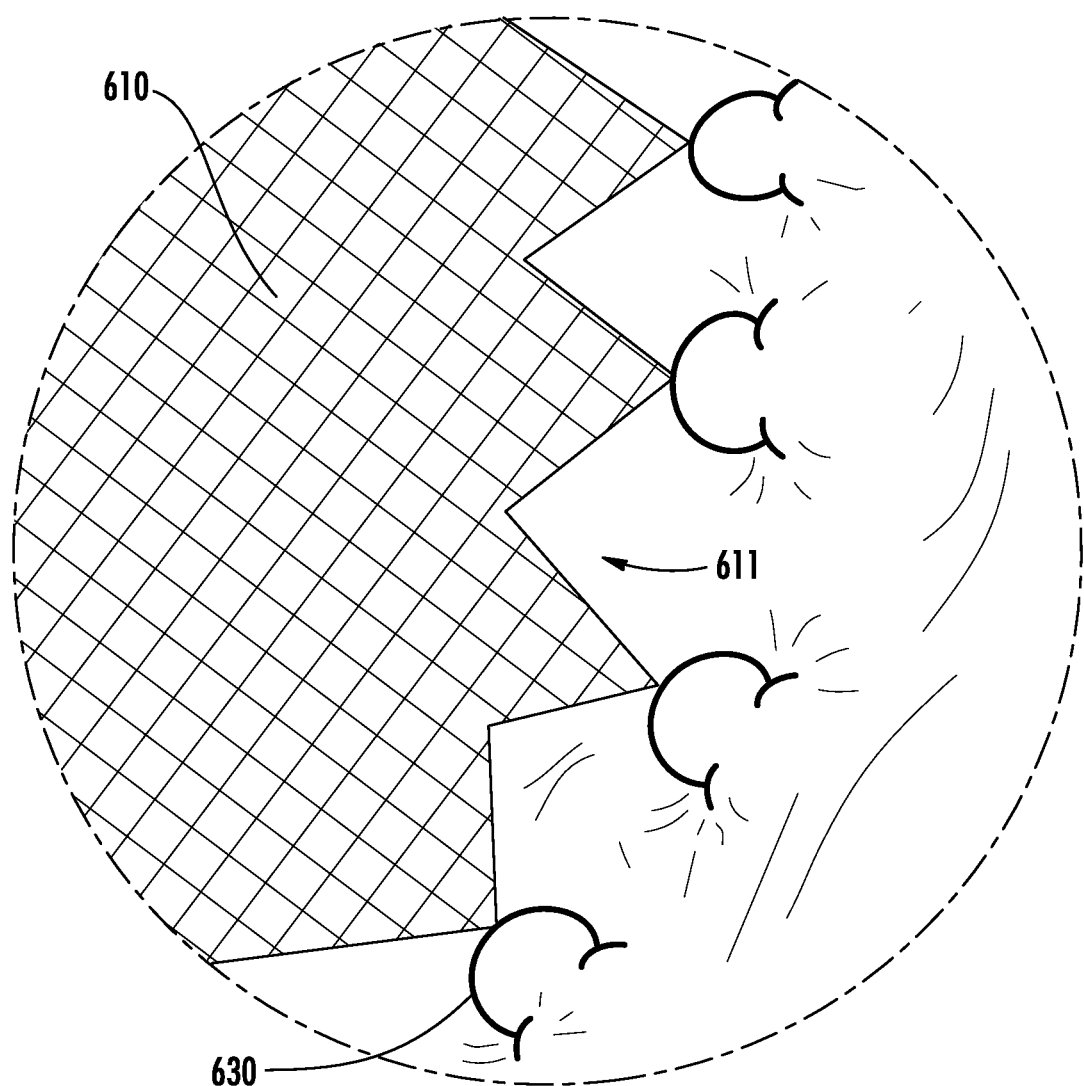
FIG. 6B illustrates a generally plan view of a detail VI B of an embodiment of a flow-regulating device as illustrated in FIG. 6A.

It will be appreciated that alternative manners of anchoring a mesh element directly to tissue, without the use of a support structure (such as illustrated in FIG. 1, FIG. 2, FIG. 3, or FIG. 4), or the fasteners 530 illustrated in FIG. 5A and FIG. 5B are within the scope and spirit of the present disclosure. For instance, as illustrated in the example of an embodiment of a flow-regulating device 600 illustrated in FIG. 6A, and in the example of a detail VI B illustrated in plan view in FIG. 6B, fasteners 630 such as barbs may be provided along the periphery 611 of a mesh element 610. Such fasteners 630 may be formed integrally as extensions of the material (e.g., wires or filaments) of the mesh element 610, or may be separately formed from and coupled to the mesh element 610.

The various flow-regulating devices disclosed herein may advantageously be used in bariatric treatments, such as gastrojejunostomies, in which flow of materials through the pylorus and into the duodenum is fully occluded or at least about 80% occluded. However, it will be appreciated that the flow-regulating capabilities of a mesh element formed in accordance with various principles of the present disclosure may be used for other treatments requiring or allowing for lower levels of occlusion. For instance, various treatments may benefit from use of a flow-regulating device formed in accordance with various principles of the present disclosure to reduce the perceived stomach volume to induce a feeling of satiety (with the resultant reduction in caloric intake) as a form of bariatric treatment. More particularly, the example of an embodiment of a flow-regulating device 700 with a mesh element 710 illustrated in FIG. 7 may be positioned proximally from the pylorus P at a desired distance to reduce the volume of the stomach S proximal to the mesh element 710. Gastric materials from the stomach S encounter the mesh element 710 before reaching the pylorus P, and are impeded from freely flowing past the mesh element 710, thus remaining for a longer period of time in the portion of the stomach S proximal to the mesh element 710. The slowing of gastric emptying has been found to have a beneficial bariatric effect, which may be achieved with placement of a mesh element 710 in accordance with principles of the present disclosure embodied in the illustrated example of FIG. 7.

As may be appreciated in view of the above, a mesh element provides various benefits compared to prior devices for regulating flow of materials. For instance, a mesh element formed in accordance with various principles of the present disclosure permits a higher degree of customization compared with prior art devices, and/or facilitates interchangeability to allow modifications during a course of treatment. Although embodiments of the present disclosure may be described with specific reference to bariatric treatments, it is appreciated that various other mesh elements may be formed in accordance with various principles of the present disclosure and used in connection with other medical treatments or procedures.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A device for regulating flow of materials through a body passage, said device comprising:
   a support structure having an open proximal end and an open distal end, wherein a lumen is defined through said support structure extending between said open proximal end and said open distal end;
   a mesh element extending across the open proximal end of said support structure and having openings therethrough selected to control flow of materials through said lumen; and
   a plurality of fasteners coupling a periphery of said mesh element to the open proximal end of said support structure.

2. The device of claim 1, wherein:
   said support structure comprises a proximal retention member at said proximal end thereof sized to inhibit migration of said flow-regulating device through the body passage; and
   said mesh element is coupled to said proximal retention member.

3. The device of claim 2, wherein said proximal retention member is formed of a first proximal wall adjacent said proximal end of said support structure and a second proximal wall distally spaced from said first proximal wall in a direction towards said distal end of said support structure.

4. The device of claim 3, wherein said mesh element is positioned and held between said first proximal wall and said second proximal wall of said proximal retention member of said support structure.

5. The device of claim 1, wherein said mesh element is sheet-like to define an upstream surface and a downstream surface with the openings defined through the mesh element to allow fluid to flow from the upstream surface, through the mesh element, and to the downstream surface.

6. The device of claim 1, wherein said plurality of fasteners is selected from the group consisting of loops, clips, barbs, and hooks.

7. The device of claim 1, wherein said plurality of fasteners comprises a plurality of loops about a periphery of said mesh element and a plurality of clips extendable through said loops and attachable to said support structure to couple said mesh element to said support structure.

8. The device of claim 1, wherein said mesh element is formed separately from said support structure.

9. The device of claim 8, further comprising at least one fastener applied to the periphery of said mesh element and to one of said proximal end or said distal end of said support structure to mount said mesh element with respect to said support structure.

10. The device of claim 1, wherein at least one of the plurality of fasteners is formed separately from said mesh element and selected from the group consisting of clips, barbs, and hooks, said plurality of fasteners extending across the periphery of said mesh element and about a periphery of said one of said proximal end or said distal end of said support structure.

11. The device of claim 1, wherein said plurality of fasteners are flexible to facilitate removal from said mesh element and said support structure to remove said mesh element from said support structure.

12. The device of claim 1, wherein said plurality of fasteners are provided on a base separately formed from said mesh element and said support structure and selectively positionable over a periphery of said mesh element and said support structure to couple said mesh element and said support structure and removable to permit removal of said mesh element from said support structure.

13. The device of claim 1, wherein said mesh element is a first mesh element having a first mesh gauge, said device further comprising a second mesh element having a second mesh gauge different from said first mesh gauge, said first mesh element being removable from said support structure and replaceable with said second mesh element to alter the flow of materials through said device and through the body passage.

14. A device for controlling flow of materials through a body passage, said device comprising:
   a mesh element having a perimeter around a concave upstream surface and a convex downstream surface; and
   a plurality of fasteners coupled about the perimeter of said mesh element and configured to engage tissue adjacent or surrounding the body passage to secure the perimeter of said mesh element to the tissue;
   wherein the mesh element defines openings therethrough extending from the concave upstream surface to the convex downstream surface of the mesh element such that material flows from the upstream surface of the mesh element to the downstream surface of the mesh element and directly therefrom to the body passage, whereby the mesh element regulates flow of materials through the body passage without another flow-regulating device such that the mesh openings are determinative of the flow of material through the body passage.

15. The device for controlling flow of claim 14, wherein said mesh element is curved to be secured within an anatomical structure upstream of the body passage with at least a periphery of said mesh element lying against the wall of the anatomical support structure.

16. The device for controlling flow of claim 15, wherein said mesh element is curved to fit within a stomach proximal to the pylorus, flow of material passing through said mesh element and to the pylorus being unimpeded.

17. The device for controlling flow of claim 14, wherein at least a portion the mesh element lies against the wall of an anatomical structure and is uncoated to allow tissue ingrowth into the mesh element.

18. A method of controlling flow of material through a pylorus, said method comprising:
- inserting a support structure through the pylorus; and
- coupling a mesh element across an opening of said support structure, said mesh element having a mesh gauge dimensioned to control flow of materials through said support structure;
- wherein material flow through the pylorus is regulated by only the mesh gauge of the mesh element without being further regulated by another flow-regulating device.

19. The method of claim 18, further comprising exchanging the mesh element with a different mesh element having a different mesh gauge.

20. The method of claim 18, further comprising:
- inserting the support structure through said pylorus before coupling the mesh element to the support structure;
- allowing the support structure to anchor within the pylorus;
- allowing material to flow through a lumen defined through the support structure; and
- coupling the mesh element to the support structure after the support structure has been anchored within the pylorus to control flow of materials through the support structure lumen and thereby to control flow of materials through the pylorus.

\* \* \* \* \*